United States Patent
Hall (10) Patent No.: US 9,597,169 B2
(45) Date of Patent: Mar. 21, 2017

(54) BRUSHHEAD FOR A POWER TOOTHBRUSH WITH A TWO POSITION COUPLING ASSEMBLY

(71) Applicant: KONINKLIJKE PHILIPS N.V., Eindhoven (NL)

(72) Inventor: Scott E. Hall, Issaquah, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 243 days.

(21) Appl. No.: 14/353,663

(22) PCT Filed: Oct. 18, 2012

(86) PCT No.: PCT/IB2012/055689
§ 371 (c)(1),
(2) Date: Apr. 23, 2014

(87) PCT Pub. No.: WO2013/061219
PCT Pub. Date: May 2, 2013

(65) Prior Publication Data
US 2014/0298603 A1    Oct. 9, 2014

Related U.S. Application Data

(60) Provisional application No. 61/551,035, filed on Oct. 25, 2011.

(51) Int. Cl.
*A61C 17/22* (2006.01)
*A46B 7/04* (2006.01)
*A46B 5/00* (2006.01)

(52) U.S. Cl.
CPC .......... *A61C 17/222* (2013.01); *A46B 5/0095* (2013.01); *A46B 7/042* (2013.01); *A61C 17/22* (2013.01)

(58) Field of Classification Search
CPC ........... A46B 7/04; A46B 7/042; A46B 7/044; A46B 13/00; A46B 13/02; A46B 13/023;
(Continued)

(56) References Cited

U.S. PATENT DOCUMENTS 3,369,265 A    2/1968    Halberstadt et al.
3,851,984 A    12/1974    Crippa
(Continued)

FOREIGN PATENT DOCUMENTS

DE    3129435    *    2/1983
EP    2184031 A1    5/2010
(Continued)

*Primary Examiner* — Mark Spisich (57) ABSTRACT

The replaceable brushhead, used for a power toothbrush, includes a neck portion (22) having a hollow part located at a proximal end thereof. The brushhead assembly includes a bristle portion (18) at a distal end of the neck portion. A connecting assembly (20) is positioned within the hollow portion of the neck, the connecting assembly having two distinct, mechanically stable, positions. In the first position, the connecting assembly has a first physical arrangement in which the brushhead assembly is conveniently removable or insertable onto an output shaft (16) from a handle portion of the power toothbrush. In the second position, the connecting assembly has a second physical arrangement, in which a portion of the connecting assembly makes physical contact with the output shaft such that the force or torque produced by the output shaft in operation is transferred to the brushhead assembly for movement thereof.

3 Claims, 7 Drawing Sheets

(58) Field of Classification Search
CPC ..... A46B 5/0095; A61C 17/22; A61C 17/222;
A61C 17/32; A61C 17/34; A61C
17/2409; A61C 17/3418; A61C 17/3445;
A61C 17/3481
USPC .......................... 15/22.1, 145, 176.1, 176.6
See application file for complete search history.

(56) References Cited

U.S. PATENT DOCUMENTS

| | | | |
|---|---|---|---|
| 4,820,154 A | | 4/1989 | Romhild et al. |
| 4,991,249 A | * | 2/1991 | Suroff ................ A46B 15/0002 15/176.2 |
| 2005/0108838 A1 | | 5/2005 | Schaefer et al. |
| 2010/0043156 A1 | | 2/2010 | Kressner |
| 2010/0101032 A1 | | 4/2010 | Kressner |
| 2010/0251493 A1 | | 10/2010 | Sale et al. |
| 2011/0107536 A1 | | 5/2011 | Dabrowski et al. |
| 2013/0255014 A1 | * | 10/2013 | Kloster ................ A61C 17/222 15/22.1 |

FOREIGN PATENT DOCUMENTS

| | | | |
|---|---|---|---|
| EP | 2263601 A1 | | 12/2010 |
| JP | 53-21650 | * | 2/1978 |
| JP | 2011506028 A | | 3/2011 |
| WO | 00/76420 | * | 12/2000 |

* cited by examiner

BRUSHHEAD FOR A POWER TOOTHBRUSH WITH A TWO POSITION COUPLING ASSEMBLY

CROSS-REFERENCE TO PRIOR APPLICATIONS

This application is the U.S. National Phase application under 35 U.S.C. §371 of International Application No. PCT/IB2012/055689, filed on Oct. 18, 2012, which claims the benefit of U.S. Provisional Patent Application No. 61/551,035, filed on Oct. 25, 2011. These applications are hereby incorporated by reference herein.

This invention relates generally to a brushhead assembly for a power toothbrush, wherein the brushhead assembly includes a connection arrangement designed for two-position operation; in one position for insertion and removal of the brushhead relative to the driveshaft from the toothbrush motor and in the other position for engagement with the driveshaft for operation of the toothbrush.

The brushhead portion of a power toothbrush typically has a much shorter useful life than the remainder of the toothbrush, i.e. the handle, which includes generally the drive, control and power assemblies of the appliance. The brushhead must be both convenient to remove and insert onto the driveshaft of the toothbrush, but also must be able to reliably transfer the force of the driveshaft to the brushhead with a minimum loss of motion. A large number of different structural arrangements have been used to accomplish these two different and somewhat conflicting requirements. In most cases, the brushhead has a single configuration which accomplishes both results, i.e. it has a tight enough fit to provide the required force transfer but which can be pulled on and off the drive member (driveshaft) with a reasonable amount of force exerted by a typical user. What is presently disclosed is a brushhead which has a connecting arrangement with two different stable physical positions, which facilitates the separate requirements of convenient insertion/removal and reliable transfer of force from the drive member.

Accordingly, the replaceable brushhead assembly for a power toothbrush having a handle portion and an output shaft for driving the brushhead disclosed herein comprises a neck portion having a hollow part at a proximal end thereof; a bristle portion at a distal end of the neck portion; and a connecting assembly positioned or positionable within the hollow part of the neck portion, the connecting assembly having two distinct, mechanically stable, different positions, including a first position in which the connecting assembly has a first physical arrangement permitting the brushhead assembly to be readily removable from or insertable onto the output shaft, and a second position in which the connecting assembly has a second physical arrangement in which the connecting assembly makes physical contact with the output shaft and is connected to the neck portion such that the output shaft force is transferred to the brushhead assembly in operation of the power toothbrush.

Figure 1:
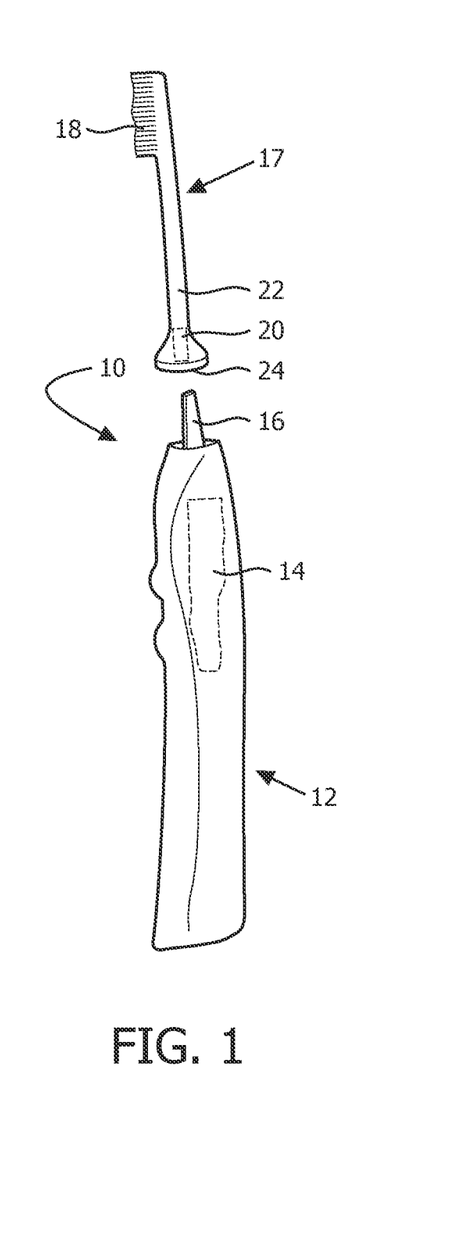
FIG. 1 is an exploded view of a power toothbrush.

FIG. 1 is an exploded view of a power toothbrush, shown generally at 10. The power toothbrush 10 includes a handle portion 12 and a drive system and a control system shown generally as a unit at 14 which are conventional in structure and operation and which can take various forms, for driving an drive/output shaft 16 with a desired motion. One example is an oscillatory motion with a frequency of approximately 260 Hz and an amplitude of approximately 10°. It should be understood that this described action is one example only and can be varied. The power toothbrush 10 also includes a removable brushhead assembly 17 which includes a set of bristles 18 at a distal end thereof. The brushhead assembly 17 is structured to be removable from the output shaft 16 when it is due for replacement. A new brushhead assembly is then inserted onto the output shaft 16 for continued operation of the toothbrush.

The present invention, as disclosed and claimed herein, is directed toward a connecting assembly 20 which fits within a neck portion 22 of the brushhead assembly 17. The connecting assembly 20 is configured and adapted to operate between two positions. In one position, a brushhead is conveniently removable from the output shaft or positionable on the output shaft, while in the second position, the brushhead assembly is firmly attached or fixed to the output shaft such that the force or torque produced by the output shaft is transferred to the brushhead assembly, preferably without any lost motion.

Figure 2A:
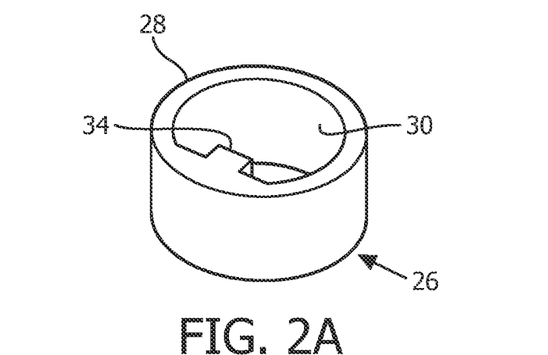
FIGS. 2A-2C are several views of a portion of one embodiment of the two position brushhead disclosed herein.
Figure 2B:
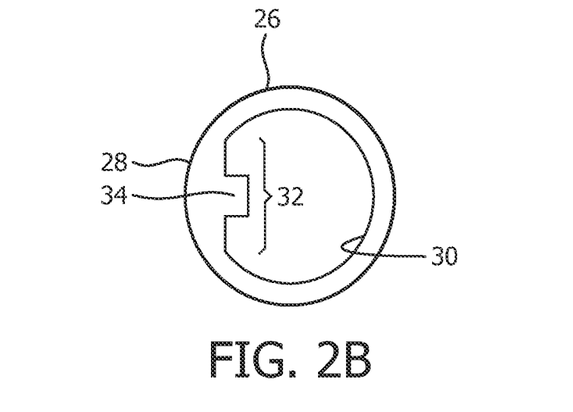
Figure 2C:
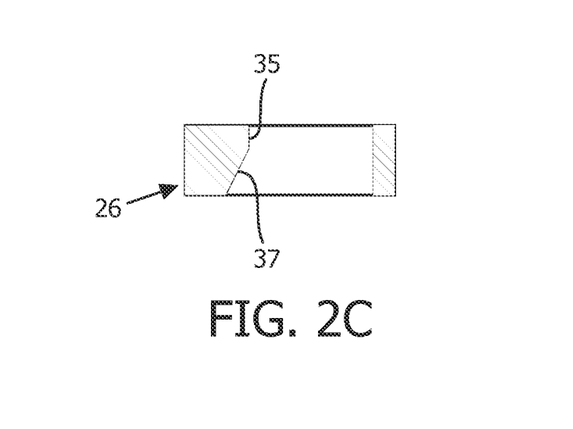
Figure 3:
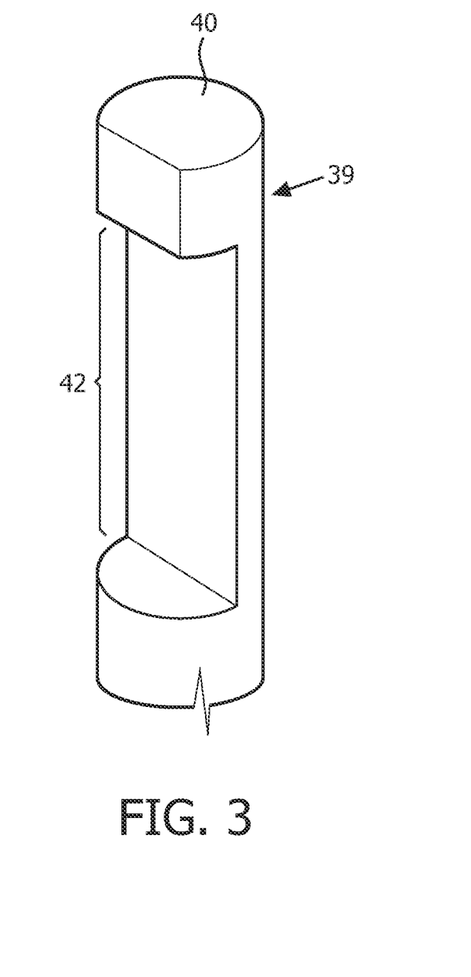
FIG. 3 is an isometric view of the drive member (shaft) configuration of the first embodiment.

The subject of this application is the brushhead assembly with the connecting assembly therein. The connecting assembly can take various arrangements, including the embodiments shown herein. FIGS. 2A-2C, 3, 4A-4C and 5A-5B show the structure and operation of a first embodiment. FIGS. 2A-2C show one part/member of the first embodiment of the connecting assembly. Member 26 is in the form of a ring which is fixedly attached to an inner surface of neck portion 22 of the brushhead, which is hollow for at least a lower part of its length from its proximal end 24. The outer surface 28 of ring member 26 mates against and has approximately the same dimension as the inner surface of neck 22. In the embodiment shown, the ring has a height of approximately 6 mm and a width (thickness) of approximately 2 mm over most of its circumference. One portion 32 of inner surface 30 of ring member 26 is flat and has a small element 34 which extends inwardly of the ring a short distance, terminating at a free end surface 35, which extends directly downwardly for a part of the height of the ring member and then angles inwardly at surface 37 over the remaining portion thereof, as shown in FIG. 2C. In the embodiment shown, this angle is approximately 60°. FIG. 3 shows another part of the first embodiment, namely a notched output shaft 39 from the handle. The output shaft includes a flat upper surface 40. A notch or cutout section 42 begins approximately 6 mm down from surface 40 and extends inwardly approximately one-half the diameter of the output shaft. The notch 42 extends downwardly of the shaft a distance of approximately 10 mm.

Figure 4A:
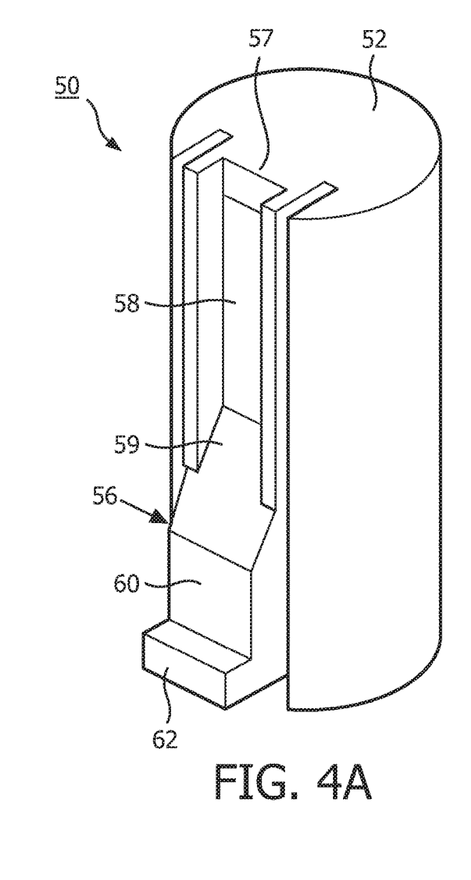
FIGS. 4A-4C are several views of a coupling assembly portion of the first embodiment.
Figure 4B:
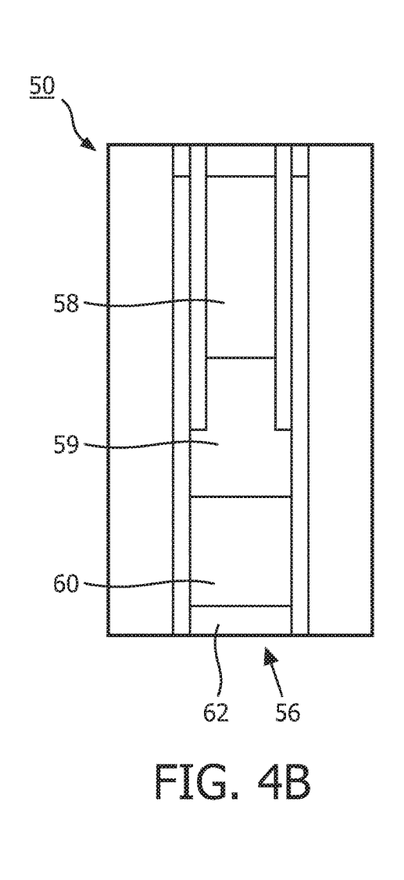
Figure 4C:
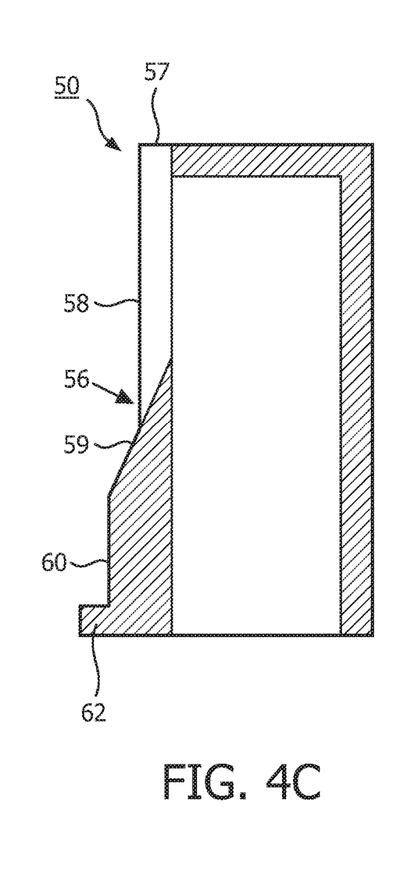

FIGS. 4A-4C show another part of the first embodiment, namely, a coupling member 50 part of the connecting assembly of the first embodiment. The coupling member fits also within the lower portion of the neck 22 of the brushhead, and is hollow, as shown most clearly in FIG. 4C, to receive output shaft 39 (FIG. 3) from the handle. The coupling member is generally cylindrical and includes a movable flap portion 56 which extends downwardly from the upper surface 52 the entire length of the coupling member, as shown most clearly in FIG. 4B. The movable portion 56 is connected to the upper surface of the coupling member by a hinge-like portion 57 which permits the movable portion to be moved inwardly of the coupling member. The movable portion includes a flat upper portion 58 which extends downwardly to an outwardly and downwardly angled portion 59 which, in the embodiment shown, has an angle of approximately 60°, which mates with the angled portion 37 of ring member 26 when the connecting assembly is in its first position. The angled portion 59 extends to another vertical flat portion 60 which ends in a small horizontally outwardly extending lip 62 which in the first position of the brushhead contacts the inner surface of the neck of the brushhead below ring 26.

Figure 5A:
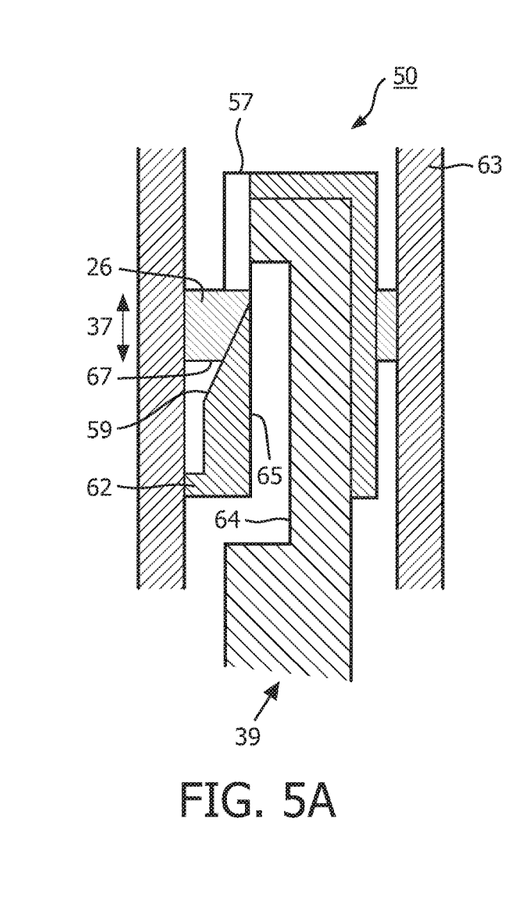
FIGS. 5A and 5B show the two operating positions (open and closed) of the first embodiment.
Figure 5B:
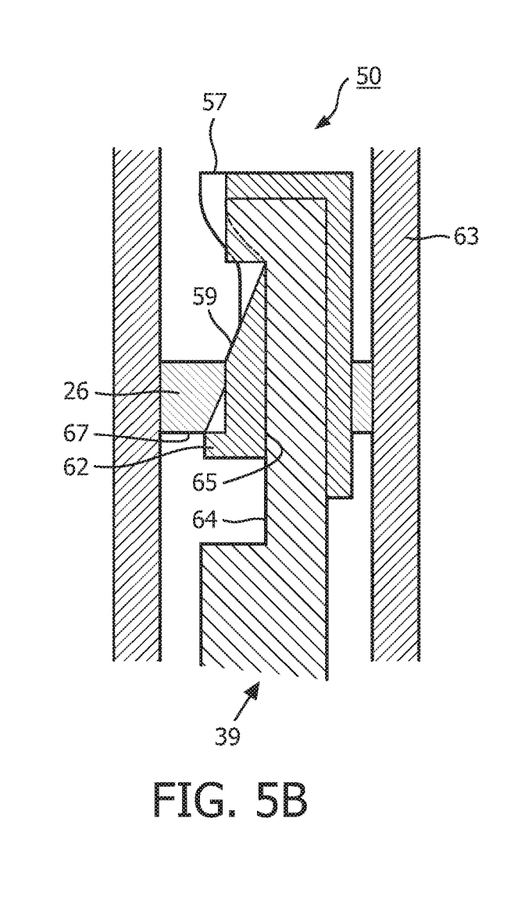

FIGS. 5A and 5B show the operation of the first embodiment. In the first position, shown in FIG. 5A, also referred to as an open position, a brushhead 63 (only a lower part is shown), along with the coupling member, is conveniently removable from the output shaft 39, and is also readily insertable onto the output shaft. In this first position, angled portion 37 of ring 26 is adjacent the angled portion 59 of the movable portion of the coupling member, with the movable portion in its outermost, i.e. rest, position, permitting the entire brushhead to be conveniently removed from the output shaft 39. When the output shaft 39 is then further pushed into the brushhead assembly, or vice versa, the angled part of the ring member moves down the angled surface 59 of the removable portion of the coupling member, forcing the movable portion inwardly against flat portion 64 of the output shaft. This movement of the output shaft into the brushhead assembly continues until the coupling member reaches the position shown in FIG. 5B, where the lower edge 67 of the ring member contacts the lip 62 of the movable portion of the coupling member. At this point, the inner surface 65 of the movable portion 56 is forced against the flat portion of the output shaft, in which position the force of the moving output shaft is transferred to the brushhead, as shown in FIG. 5B. When the brushhead is to be removed, the brushhead is simply pulled away from the handle, allowing the movable portion of the coupling assembly to return to its rest position, as shown in FIG. 5A, which allows the brushhead assembly to be easily removed.

Figure 6A:
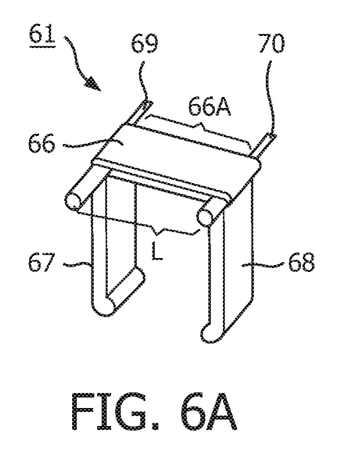
FIGS. 6A-6C are various views of the structure and operation of a second embodiment of the two-position brushhead.
Figure 6B:
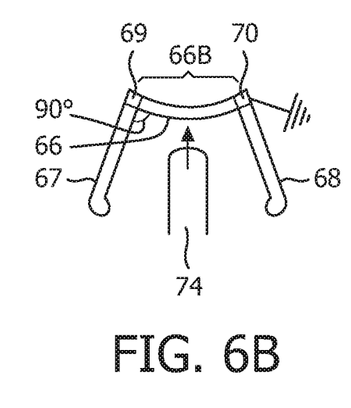
Figure 6C:
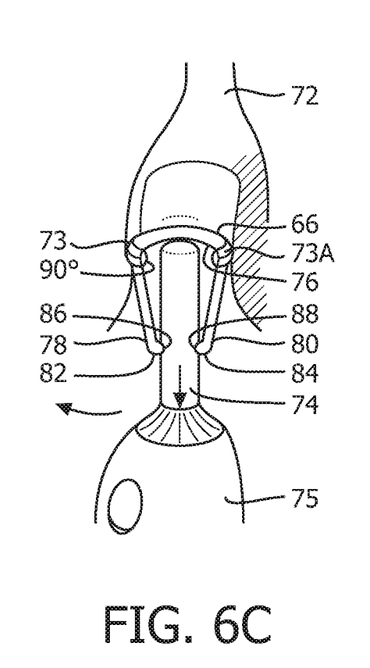

FIGS. 6A-6C show a second embodiment of a connecting assembly for a two-position brushhead assembly, the connecting assembly being positioned in the lower portion of the neck of the brushhead assembly. FIG. 6A shows a connecting assembly 61 which includes a top portion 66 having a length 66A and spaced end portions 67 and 68 which extend downwardly from top portion 66 at an angle A of 90° relative to the top portion. The top portion is connected to the end portions by two pins 69 and 70. The connecting member is arranged and constructed so that top portion 66 flexes between two positions, a concave position in which the top portion bends inwardly (FIG. 6B), and a convex position in which the top portion bends outwardly (FIG. 6C). The connecting member can be made from a flexing plastic or metal. FIG. 6B shows the connecting member in its first, convex, position, in which position the distance between the two pins 69 and 70 is 66B, which is less than 66A. The top portion 66 fits within the opening of neck portion 72 of the brushhead assembly when the top portion is in its convex position in which distance 66B between the pins 68 and 70 is just wide enough to fit in the opening in the neck portion. The dimensions of the top portion will vary depending on the size of the neck opening. In one example, the top portion is 10 mm long and 4 mm wide. When connecting member 61 is inserted into the neck portion (in its FIG. 6B position), the two pins 68 and 70 are captured in mating slots 73, 73A in the inside surface of neck 72. The neck 72 extends to the remainder of the brushhead assembly (not shown). The angle between the top portion and each of the two end portions is still 90°. The brushhead assembly is provided for use with the inserted connecting member in the position of FIG. 6B.

When the brushhead assembly is to be moved onto the handle, the output shaft 74 from handle 75 is moved against the undersurface 76 of the top portion 66. The two end portions move toward each other and the top portion snaps into its second, convex position, as shown in FIG. 6C. In this position, there remains a 90° angle between the top portion and each of the two end portions, respectively. As the output shaft moves against the under surface of the top portion, the top portion snaps into its second position. The distal ends 78, 80 of the end portions have small protuberances 82 and 84, which move into detents 86 and 88 in the output shaft. In this position, the brushhead is firmly fixed to the output shaft and the force of the movement of the output shaft is transferred to the brushhead assembly. When the brushhead assembly is to be removed, the output shaft is pulled slightly away from the brushhead, forcing the two end members outwardly, so that the top portion of the connecting assembly snaps back into its concave position. The brushhead can then be conveniently and easily removed from the output shaft.

Figure 7A:
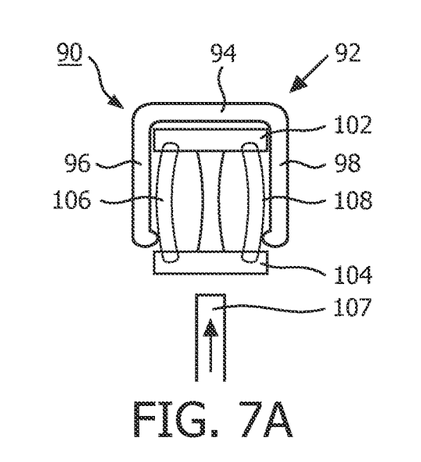
FIGS. 7A-7C are various views of the structure and operation of another embodiment of the two-position brushhead.
Figure 7B:
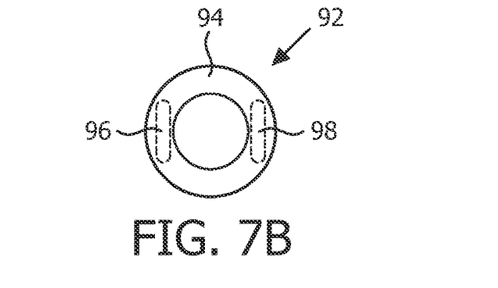
Figure 7C:
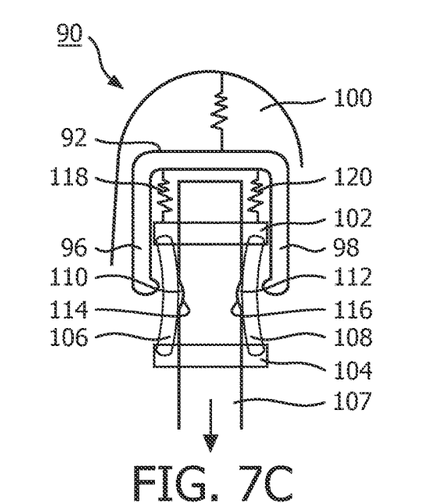

FIGS. 7A-7C show a further embodiment involving a spring arrangement in a connecting assembly which fits within the lower part of the neck of a brushhead assembly. The connecting assembly, shown generally at 90, includes a cylindrical upper member 92 having a diameter which fits within the neck of the brushhead. The upper member 92 includes a top ring-like portion 94 and two depending leg members 96 and 98 (FIG. 7B). The upper member is connected to an inner portion of the neck of the brushhead by a vertical spring 100. The connecting assembly includes a coupling assembly which includes upper and lower flat plate portions 102, 104, each of which has a central opening which allows an output shaft 107 from the handle of the toothbrush to extend therethrough, as shown in FIG. 7C. The upper plate 102 contacts the two leg members 96 and 98 of the upper member, while the lower plate is configured to contact the inner surface of the hollow neck portion of the brushhead. Positioned between the two plate portions 102 and 104 are two springed elements 106 and 108, which in one position are bowed outwardly (concave), as shown in FIG. 7A, when the brushhead assembly is apart from the output shaft 107. As the output shaft moves into the coupling assembly, the two springed elements snap into their second position, as shown in FIG. 7C. The springed elements including protruding portions 110, 112 which extend toward each other from the inner surfaces of the springed elements and contact detents 114, 116 in the opposite sides of the driveshaft. In this position of the connecting assembly, the brushhead is held firmly against the output shaft, such that the force produced by the output shaft is transferred to the brushhead.

Two springs 118 and 120 connect upper plate 102 to the upper member 92 so that as the output shaft is pulled out of the brushhead, when the brushhead is to be replaced, the two spring members 106 and 108 snap back into their first position, and the coupling member remains attached to the connecting assembly and within the brushhead, i.e. the coupling member does not pull away from the brushhead.

Various embodiments have been shown and described which define a brushhead having a connecting assembly therein which moves between two positions, as the output shaft (driveshaft) from the handle is inserted into the brushhead. In one position, the connecting assembly is arranged and configured so as to conveniently permit the brushhead to be removed from the output shaft, and also to permit a brushhead to be inserted onto the output shaft. In a second position, the coupling portion of the connecting assembly comes into mechanical contact with the output shaft in such a manner that the torque force produced by the output shaft is transferred to the brushhead, with little or no lost motion.

Although a preferred embodiment of the invention has been disclosed here for the purposes of illustration, it should be understood that various changes, modifications and substitutions may be incorporated in the embodiment without departing from the spirit of the invention, which is defined by the claims which follow.

The invention claimed is:

1. A replaceable brushhead assembly for a power toothbrush having a handle portion and an output shaft for driving the brushhead, comprising:
   a neck portion having a hollow part at a proximal end thereof;
   a bristle portion at a distal end of the neck portion; and
   a connecting assembly positionable within the hollow part of the neck portion, the connecting assembly having at least two distinct, different physical positions, including a first distinct physical position, and a second distinct physical position
   wherein the connecting assembly comprises (i) a coupling member having a movable flap portion extending along a portion of the length of the outer surface of one side of the coupling member, the movable flap portion connected to an upper surface of the coupling member by a hinge-like portion, the movable portion having a flat upper portion extending downwardly to an angled portion extending to a second flat portion having a horizontally outwardly extending lip;
   (ii) a hollow ring member having an outer surface which mates against an inner surface of the neck portion of the brush head securing the connecting assembly against the inside of the brush head, the ring member having an inwardly extending element along a portion of an inner surface thereof, the inwardly extending element having an angled portion along a part of a length thereof;
   wherein when the connecting assembly is in the first distinct position, the angled portion of the ring member is adjacent the angled portion of the movable flap of the coupling member, permitting the brush head assembly to be readily removable from or insertable onto the output shaft, and when the connecting assembly is in the second distinct position, the angled portion of the ring member presses against the flat upper portion of the coupling member, moving a flat inner surface of the movable flap portion of the coupling member into tight physical contact with a flat portion of a notch in the output shaft in such a manner that a force of the output shaft is transferred to the brushhead assembly in operation of the power toothbrush.

2. The brushhead assembly of claim 1, wherein the connecting assembly comprises the coupling member into which the output shaft fits and the ring member fixed to an inner surface of the hollow part of the neck portion, which makes contact with the outer surface of the coupling member, forcing and maintaining the flat inner surface of the movable flap portion of the coupling member into tight physical contact with the flat portion of the notch in the output shaft, as the output shaft is moved into the coupling member when the brushhead is inserted onto the output shaft, from the first distinct physical position to the second distinct physical position of the connecting assembly.

3. The brushhead assembly of claim 1, wherein the connecting assembly comprises the ring member permanently attached to and extending inwardly of an inner surface of the neck portion and the coupling member making slidable contact with the inner surface of the neck portion and wherein the ring member is arranged (a) in the second distinct physical position to mate with a corresponding mating portion of the movable flap portion of the coupling member to produce and maintain a tight physical contact between the flat inner surface of the movable flap portion of the coupling member and the flat portion of the notch in the output shaft and (b) in the first distinct physical position to permit the brush head assembly to be removed from or inserted onto the output shaft.

\* \* \* \* \*